United States Patent [19]

Poverenny et al.

[11] 3,981,772

[45] Sept. 21, 1976

[54] METHOD OF ATTENUATING VIRUSES WITH SIMULTANEOUS STABILIZATION OF THEIR ANTIGENS USING SELECTED AMINOMETHYLOL COMPOUNDS

[76] Inventors: Alexandr Mikhailovich Poverenny, ulitsa Kurchatova, 22-a, kv. 52; Jury Alexeevich Semin, Ulitsa Zholio-Kjuri, 60, Kv. 41, both of Obninsk Kaluzhskoi oblasti; Mikhail Petrovich Chumakov, Leninsky prospekt, 68/10, kv. 354, Moskow; Antonina Vasilievna Gagarina, poselok Instituta poliomielita, 3, kv. 30; Maria Kronidovna Khanina, poselok Instituta poliomielita, 3, kv. 16, both of Moskovskaya oblast; Evgeny Alexandrovich Tkachenko, ulitsa Yablochkova, 23, kv. 216; Vyacheslav Nikolaevich Bashkirtsev, ulitsa arkhitektora Vlasova, 33, korpus 1, kv. 23, both of Moscow, all of U.S.S.R.

[22] Filed: July 17, 1975

[21] Appl. No.: 596,909

[30] Foreign Application Priority Data
Aug. 27, 1974 U.S.S.R............................ 2055851

[52] U.S. Cl.................................................. 195/1.4
[51] Int. Cl.².......................................... C12K 7/00
[58] Field of Search........................................ 195/1.4

[56] References Cited
UNITED STATES PATENTS

| | | | |
|---|---|---|---|
| 3,197,372 | 7/1965 | Schafer et al. | 195/1.4 |
| 3,456,053 | 7/1969 | Crawford | 195/1.4 |

*Primary Examiner*—Sam Rosen
*Attorney, Agent, or Firm*—Lackenbach, Lilling & Siegel

[57] ABSTRACT

A method of attenuating viruses with a simultaneous stabilization of their antigens which consists in inactivating viruses with an aminomethylol compound having the formula

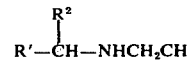

where
R' is H, $CH_2OH$, COOH;
R² is H, $(CH_2)_nCH_3$, $(CH_2)_nNH_2$, $(CH_2)_nCOOH$ or $(CH_2)_nOH$; and
N is an integer of 1–4, said compound being in a concentration of from $6.6 \times 10^{-3}$ to $1.6 \times 10^{-3}$ mole at a temperature from 4° to 32°C is disclosed.

This method can be used to prepare standard and reliable prophylactic attenuated viral vaccines and diagnostic preparations especially useful against dangerous viral diseases.

2 Claims, No Drawings

METHOD OF ATTENUATING VIRUSES WITH SIMULTANEOUS STABILIZATION OF THEIR ANTIGENS USING SELECTED AMINOMETHYLOL COMPOUNDS

BACKGROUND OF THE INVENTION

1. Field of the Invention

This invention relates to the biological industry (medical and veterinary), and more particularly, it relates to a method of preparing attenuated viral preparations that retain specific antigen properties, useful in prophylaxis or laboratory diagnosis. Still more particularly, this invention relates to a method of attenuating the infectiousness of viruses with a simultaneous stabilization of their antigens.

2. Description of the Prior Art

It is known that specific antigenic properties of viruses are connected with protein macromolecules of viral membranes, while the infectiousness (that is, the infecting power) depends on a nucleic acid which is present at the center of the virus. It is known also that for preparing attenuated (devoid of infectious activity) viral preparations, suitable, for example for prophylactic vaccination against viral diseases or for safe use in diagnostic serological reactions, it is necessary to destroy the structure of the nucleic acid of the virus, and at the same time to protect viral proteins, the carriers of specific antigenic and immunogenic properties, against undue denaturation and to stabilize them as well. The processes of attenuating infectiousness and stabilizing antigen viral proteins should take place simultaneously.

When placed in a suspension of cells of affected tissues, or cell-free substrate, pathogenic viruses, for example, the causative agents of encephalitis and hemorrhagic fever, are usually destroyed by themselves at temperatures above the water freezing point. The rate of inactivation is different in various viruses (with consideration of the protective action of some substrates containing the viruses), but in general, it is proportional to the elevation of the temperature. The loss of infection power under the action of temperatures, is, as a rule, accompanied by a progressive decrease in the antigenic properties of the preparation and the complete loss of same. In this connection, methods of attenuation of infectiousness of viruses, which make it possible at the same time to protect their antigens from excess reduction in activity with increasing temperature, are used. These methods stabilize virus protein antigens and prevent their destruction. For example, known in the prior art are methods of chemical treatment of a viral preparation with phenols, beta-propiolactone, and formaldehyde, in combination with a more or less short duration of temperature on the order of 37°, 32°, 24°, and 4°C, depending on the nature of the virus (cf. Gard, S., Chemical Inactivation, "Nature of Virus," Moscow, 1958).

The process of virus inactivation should be carried out under conditions which completely destroy virus infectiousness with preservation of their maximum antigenic properties none of which can be attained with the above-named chemical substances.

For example, formaldehyde is most often used as an inactivator of viruses in the manufacture of vaccines against viral encephalitis and hemorrhagic fever. It is used in a concentration from $2.4 \times 10^{-2}$ to $6 \times 10^{-3}$ M, depending on the substrate containing the virus. Its optimum dose is difficult to select and this results in excess denaturation of antigen proteins and reduction of the final preparation's immunogenicity. When treated with formaldehyde in said concentrations, the antigens used for the complement fixation test, become anticomplementary. Therefore, they cannot be used in the test.

Another disadvantage of using formaldehyde as an inactivating agent concerns the length of the inactivation process which is detrimental to the immunogenic activity of vaccine.

In order to compensate for the inevitable loss of antigenic activity of the viral preparation due to the destructive effect of formaldehyde, the concentration of the virus in the material should be very high, which is difficult to attain under conditions of an industrial enterprise. Moreover, the presence of free formaldehyde in the vaccine produces pain in those vaccinated; accordingly special deformalinization of vaccine is necessary.

SUMMARY OF THE INVENTION

The primary object of the invention is to use this selective action of a suitable inactivator of infectiousness of the of nucleic acid of the virus with simultaneous protection from destruction of the antigenic and immunogenic properties thereof.

Another object of this invention is to develop a method of attenuating viral infectiousness that would ensure reliable inactivation of the viral preparation.

Another object of this invention is to develop a method of attenuating viral infectiousness in order to significantly accelerate the process of viral attenuation.

Yet another object of this invention is to provide a method of attenuating viruses in order to make it possible to prepare vaccines of better quality that could be used for longer periods of time.

Still another object of this invention is to provide a method of attenuating viruses, which produce encephalities and hemorrhagic fever, that would ensure safe and highly immunogenic standard vaccines and diagnostic preparations useful against these dangerous infections in man.

Finally, another object of this invention is to search for an attenuating agent that would make it possible to destroy or modify the nucleic acid of the virus — the carrier of infectious power and which would also preserve the antigenic and immunogenic properties of the virus.

These and other objects have been attained in accordance with a method comprising attenuation of a liquid virus-containing material isolated from cell detritus with an aminomethylol compound having the formula I $$R^1-\underset{\underset{R^2}{|}}{CH}-NHCH_2OH \qquad (I)$$

where
$R^1$ is H, $CH_2OH$ or COOH;
$R^2$ is H, $(CH_2)_nCH_3$, $(CH_2)_nNH_2$, $(CH_2)_nCOOH$ or $(CH_2)_nOH$; and
N is an integer of 1 – 4 said compound being in concentration of from $6.6 \times 10^{-3}$ to $1.6 \times 10^{-3}$ M at a temperature from 4° to 32°C, said temperature being selected depending on the nature of the virus and the purpose of the preparation, at an exposure s temperature from 4° to 32°C for a period of time sufficient to attenuate the infectiousness of the virus.

The whole process of attenuating the infectiousness of the virus is carried out under sterile conditions with an obligatory pre checking of the virus-containing liquid for the absence of contaminants (microorganisms, fungicides, etc.).

After inactivation, the obtained material is experimentally tested for safety (i.e., for the presence of live virus) in susceptible animals, as well as for immunologic and antigenic activity. If the tests give favorable results, the obtained material is considered suitable for use as a vaccine or as a diagnostic antigen in serological reactions.

The method of this invention is characterized by (1) good reproducibility of results, (2) it does not require any special apparatus. and (3) can be realized on an industrial scale.

The main advantages of the instant invention are the following:

1. The invention ensures radical improvement in the process for preparing various prophylactic and diagnostic viral preparations, for example, against a wider variety of dangerous viral encephalitis and hemorrhagic fevers, and also for accumulation of harmless (for the laboratory personnel) stabilized diagnostic antigens of the causative agents of above-named infections.

2. The possibility of a regular issue of standard highly immunogenic batches of prophylactic attenuated viral vaccines and viral antigens — causative agents of especially dangerous infections.

3. High reliability of the obtained vaccines and diagnostic preparations, since the aminomethylol compounds quickly and irreversibly destroy viral infectiousness.

4. The possibility of a long shelf-life of the obtained vaccines without impairment of their immunological activity, since the immunogenic and antigenic properties are stabilized.

The results of the experimental tests of the proposed method of attenuating viruses and stabilization of their antigens have been shown on two viruses, namely, tick-borne encephalitis virus grown on chick embryo tissue culture and the virus of the Crimean hemorrhagic fever multiplied in the brain of infected new-borne albino mice. These viruses were inactivated with monomethylol lysine. Prepared were immunogenic preparations exhibiting sufficiently high immunological resistance in vaccinated albino mice (against tick-borne encephalitis), suitable for immunization of animal donors of hyperimmune globulins (against the Crimean hemorrhagic fever) and useful as antigens in the complement fixation test.

Table 3 gives the data on the dynamics of attenuation of tick-borne encephalitis virus in one batch of cell-free virus-containing liquid by the action of formaldehdye and monomethylol lysine at a temperature of 32°C. This positively demonstrates the superiority of monomethylol lysine.

Table 3

| Attenuating agent taken in concentration, in M | Exposure, in hours | | | | | | | |
|---|---|---|---|---|---|---|---|---|
| | 0 | 6 | 12 | 18 | 24 | 36 | 48 | 72 |
| | virus concentration ($LD_{50}$, in ml) | | | | | | | |
| 1. Formaldehyde, $6\times10^{-3}$ | 5.6 | 4.0 | 3.6 | 3.5 | 3.0 | 2.0 | 0.7 | 0 |
| 2. Monomethylol | | | | | | | | |

Table 3-continued

| Attenuating agent taken in concentration, in M | Exposure, in hours | | | | | | | |
|---|---|---|---|---|---|---|---|---|
| | 0 | 6 | 12 | 18 | 24 | 36 | 48 | 72 |
| | virus concentration ($LD_{50}$, in ml) | | | | | | | |
| lysine, $3.3\times10^{-3}$ | 5.6 | 2.0 | 1.1 | 0.7 | 0 | 0 | 0 | 0 |

The concentration of the virus is expressed in logarithms of the terminal titre of the virus as determined in experiments on albino mice weighing 5–6 g, previously infected with the virus before and during the process of attenuation.

Table 3 shows that the titre of the tick-borne encephalitis virus drop sharply, i.e., as early as 6, 12, and 18 hours under the effect of monomethylol lysine, and that the virus is fully attenuated as early as 24 hours after initiation of the experiment. At the same time, formaldehyde fails to inactivate the virus fully in 48 hours. Both batches of attenuated virus (with formaldehyde and monomethylol lysine) are kept at 32°C for 72 hours and then used for vaccination of albino mice by common conventional methods.

The test of the immunological resistance in two groups of vaccinated mice has shown that the vaccine prepared with the aminomethylol compound has sufficient immunogenicity, its index being 4.0, while the vaccine prepared with formaldehyde has an index of 29 and does not meet immunogenic standards. It follows therefore, that treatment of said virus with the aminomethylol compound at a temperature of 32°C attenuates infectiousness of the virus within 24 hours, and also stabilizes its antigen against the harmful action of elevated temperature with preservation of the immunogenic properties of the preparation, even after three days of treatment. Under these conditions, formaldehyde treatment significantly reduces the immunogenic properties of the viral preparation of the same batch.

Table 4 gives the results of testing the preparation of tick-borne encephalitis virus attenuated with monomethylol lysine and formaldehyde, for developing immunity to tick-borne encephalitis (the preparation was treated at a temperature of 32°C for 72 hours). The results of the test are expressed in in indices of immunological resistance in mice.

Table 4

| Test No. | Monomethylol lysine concentration | | | Formaldehyde in concentration of $6\times10^{-3}$M |
|---|---|---|---|---|
| | $1.6\times10^{-3}$M | $3.3\times10^{-3}$M | $6.6\times10^{-3}$M | |
| 1 | 5.4 | 5.8 | 5.5 | 4.8 |
| 2 | 5.0 | 4.6 | 3.7 | 3.1 |

The tabulated data shows that attenuation of tick-borne encephalitis virus with monomethylol lysine solutions of three different concentrations in two experiments gives highly immunogenic vaccines in five out of the six cases, while attenuation with formaldehyde in one experiment does not meet the standard requirements.

The results of attenuation of the tick-borne encephalitis virus with monomethylol lysine at a concentration at $3.3\times10^{-3}$m at 32°C for 48 hours and 72 hours are given in Table 5.

Table 5

| Experiment No. | Exposure time, hrs | Presence of virus in preparation after attenuation | Index of resistance of vaccinated mice | Compliance with standard |
| --- | --- | --- | --- | --- |
| 1 | 48 | 0 | 6.2 | + |
|   | 72 | 0 | 6.2 | + |
|   | 48 | 0 | 6.4 | + |
| 2 | 72 | 0 | 6.4 | + |
| 3 | 48 | 0 | 6.5 | + |
|   | 72 | 0 | 6.3 | + |

Table 5 shows the tick-borne encephalitis virus is completely attenuated. In all cases, immunogenicity of the vaccine is very high and the vaccines comply with the standard requirements. This data illustrates the possibility of regular preparation of vaccines of very high quality with aminomethylol compounds.

Reproducibility of the process for preparing highly immunogenic vaccines is illustrated in Table 6. Out of 21 vaccines prepared with monomethylol lysine, only one batch proved to be unacceptable. The characteristics of immunogenicity expressed in resistance indices are given in Table 6.

Table 6

| Number of batches of vaccine against tick-borne encephalitis | Resistance index, IR (lg $LD_{50}$) | | | | |
| --- | --- | --- | --- | --- | --- |
|  | 3.0–3.9 | 4.0–4.9 | 5.0–5.9 | 6.0–6.9 | 7 |
| 21 | 1* | 6 | 4 | 8 | 2 |

*National standard requirements: vaccine is considered immunogenic if its resistance index is 4.0 or above.

Table 7 gives the data on the stability of the vaccine against tick-borne encephalitis during storage at a temperature from +4° to +6°C. Immunogenicity is expressed in the same units as in Table 6.

Table 7

| Experiment No. | Monomethylol lysine concentration, M | Resistance index, IR | Storage (months) | Resistance index after storage, IR |
| --- | --- | --- | --- | --- |
| 1 | $6.6\times10^{-3}$ | 5.5 | 14 | 6.1 |
| 2 | $3.3\times10^{-3}$ | 5.8 | 14 | 6.5 |
| 3 | $1.6\times10^{-3}$ | 4.6 | 14 | 4.5 |

Table 8 illustrates the dynamics of attenuation of the crimean hemorrhagic fever (Hodge's strain) via monomethylol lysine, at a temperature of 24°C.

Table 8

| Exposure, hr. | Control | Virus titre in lg $LD_{0.02}$/ml | | | |
| --- | --- | --- | --- | --- | --- |
|  |  | formaldehyde | | monomethylol lysine | |
|  |  | $1.5\times10^{-3}$M | $3\times10^{-3}$M | $1.6\times10^{-3}$M | $3.3\times10^{-3}$M |
| 0 | 5.1 |  |  |  |  |
| 12 | 4.5 | 3.2 | 3.16 | 1.8 | 1.36 |
| 24 | 3.66 | 1.65 | 0.7 | 0 | 0 |
| 36 | 2.8 | 0 | 0 | 0 | 0 |

The virus-containing material is a 10 per cent suspension of newborn-mice brain infected with the virus of the Crimean hemorrhagic fever. The rate of attenuation of the virus under the effect of monomethylol lysine is significantly higher than that observed with formaldehyde. The direct dependence of the attenuation degree on the concentration of the attenuating agent is established. This data on the attenuation of the Crimean hemorrhagic fever virus agrees with the results of the experiments run on the attenuation of tick-borne encephalitis virus, and further supports the advantage of using the present aminomethylol compounds over formaldehyde.

Table 9 discloses data on the titres of the antigens of the Crimean hemorrhagic fever virus in the complement fixation test, before and after treatment with monomethylol lysine and formaldehyde at a temperature of 4° or 24°C. It has been shown that treatment with monomethylol lysine in a concentration of $3.3\times10^{-3}$M does not give anticomplementary properties, nor does it significantly reduce the degree of antigen specific activity in complement fixation test. These observations indicate possible manufacture of stabilized antigens attenuated with aminomethylol compounds for the complement fixation test from the Crimean hemorrhagic fever.

From the experimental data it follows that attenuation of viral infectiousness in said virus-containing materials is much more effective with the present aminomethylol compounds than with formaldehyde, a feature which opens new prospects for improving the methods of manufacturing attenuated prophylactic vaccines and diagnostic virus antigens.

Table 9

| Antigen | Antigen titres in complement fixation test | | | | |
| --- | --- | --- | --- | --- | --- |
|  | before treatment | treatment at +4°C | | treatment at +24°C | |
|  |  | formaldehyde | monomethylol lysine | formaldehyde | monomethylol lysine |
| Experiment 1 | 1:32 | 1:32 | 1:32 | 1:16 | 1:16 |
| Experiment 2 | 1:32 | 1:6 | 1:32 | 1:8 | 1:16 |
| Experiment 3 | 1:64 | 1:64 | 1:64 | 1:32 | 1:32 |
| Experiment 4 | 1:32 | — | — | 1:32 | 1:32 |

For a better understanding of the invention, the following examples of its practical embodiment are given by way of illustration only.

EXAMPLE I

PREPARATION OF VACCINE AGAINST TICK-BORNE ENCEPHALITIS

A virus-containing culture fluid used in the experiment of the harvest of tick-borne encephalitis virus is grown on an infected tissue culture of chick embryo in a nutrient medium No. 199. The incubation was continued for three days at a temperature of 37°C.

The obtained virus-containing culture fluid was centrifugally separated at 9000 rpm, then passed through clarifying asbestos plates and finally through filters having a pore size of 450 nm.

To the thus purified* filtrate there was added an attenuating agent in the form of a freshly prepared solution of monomethylol lysine. The solution was prepared as a 0.7 M solution of lysine in a 0.1 M sodium phosphate buffer to which there was added formaldehyde (40 per cent solution, i.e. 13.3 M aqueous solution).

*The preparation can be separated from the cell detritus either before or after virus attenuation.

The end concentration of monomethylol lysine in the solution was 0.166 M, lysine excess was 0.54 M; the pH of the solution was 6.8; and free formaldehyde was absent in the solution.

Said solution of monomethylol lysine was added in a quantity of 20 ml per liter of pure virus-containing liquid, which corresponded to the end concentration of $3.3 \times 10^{-3}$M of monomethylol lysine. The attenuation was effected at a temperature of 32°C for 48 hours.

The biological control proved the absence of live virus and the acceptable immunological activity of the preparation. The preparation was proved suitable for use as a vaccine.

EXAMPLE II

PREPARING NONINFECTIOUS ANTIGEN OF CRIMEAN HEMORRHAGIC FEVER VIRUS FOR COMPLEMENT FIXATION TEST

The substrate containing the Crimean hemorrhagic fever virus for preparing an antigen for the complement fixation test was a 10% suspension of a brain tissue of newborne albino mice on a borate buffer having a pH of 9.0. The suspension was clarified by centrifuging at 13,000 rpm for 30 minutes.

In order to remove host cell components from the centrifugate, use was made of protamine sulphate in the end concentration of 1.0 mg/ml. The mixture was allowed to stand for 2 hours at a temperature of 4°C with periodically shaking. The precipitate was separated by centrifuging at 3000 rpm for 15 minutes.

The supernatant solution containing the Crimean hemorrhagic fever virus was mixed with a solution of monomethylol lysine prepared in accordance with Example 1, in a quantity of 20 ml per liter of the virus-containing liquid. This corresponds to a $3.3 \times 10^{-3}$M concentration of monomethylol lysine. The mixture was kept for 24 hours at a temperature of 24°C.

The obtained preparation was successfully used as an antigen in the complement fixation test (See Table 9).

What we claim is:

1. A method of attenuating the infectiousness of viruses with a simultaneous stabilization of their antigens which consists of attenuating a liquid virus-containing material with an aminomethylol derivative having the formula:

$$R'-\overset{R^2}{\underset{|}{C}H}-NHCH_2OH$$

where:
R' is H, $CH_2OH$ or COOH;
R$^2$ is H, $(CH_2)_2CH_3$, $(CH_2)_nNH_2$, $(CH_2)_nCOOH$ or $(CH_2)_nOH$; and
N is an integer of 1 – 4
said compound being in a concentration of from $6.6 \times 10^{-3}$ to $1.6 \times 10^{-3}$M at a temperature from 4° to 32°C, the selection of the temperature depending on the nature of the virus, and the exposure being sufficient for a complete attenuation of viral infectiousness.

2. The method of claim 1, wherein said compound is monomethylol lysine.

* * * * *